United States Patent [19]
Turro

[11] 3,959,642
[45] May 25, 1976

[54] INCENSE LAMP
[75] Inventor: Jerome C. Turro, Riverdale, N.Y.
[73] Assignee: Lawrence Peska Associates, Inc., New York, N.Y. ; a part interest
[22] Filed: Feb. 6, 1975
[21] Appl. No.: 547,721

[52] U.S. Cl. .............................. 240/2 LC; 21/116; 21/120
[51] Int. Cl.² ...................... F21V 33/00; A61L 9/02
[58] Field of Search ................ 240/2 R, 2 HT, 2 G, 240/2 LC, 1 LP, 10 R, 1 EL, 47; 21/110, 116, 117, 120, 122, 119

[56] References Cited
UNITED STATES PATENTS

| 1,357,824 | 11/1920 | Rhodes et al. ..................... 240/2 LC |
| 1,547,160 | 7/1925 | Bailey ................................ 240/2 LC |
| 1,732,707 | 10/1929 | Winsboro .......................... 240/2 LC |
| 2,742,342 | 4/1956 | Dew et al. ......................... 21/119 X |
| 2,761,055 | 8/1956 | Ike .................................... 21/120 X |
| 3,080,624 | 3/1963 | Weber ............................... 21/119 X |

FOREIGN PATENTS OR APPLICATIONS

| 570,158 | 1/1924 | France ................................ 21/117 |
| 627,050 | 5/1927 | France ............................. 240/2 LC |
| 557,789 | 5/1923 | France ............................. 240/2 LC |

Primary Examiner—Joseph F. Peters, Jr.
Attorney, Agent, or Firm—Richard E. Nanfeldt

[57] ABSTRACT

An incense lamp consisting of a base communicating with an upward extending transparent housing. A light bulb and socket are mounted in a housing mounted onto the base, wherein the light socket housing is entirely disposed within the transparent housing. A power source with switch communicates with the electrical light socket. Air passage tubes allow passage of cold air into the chamber defined by transparent housing. A cover assembly containing a liquid holding cup communicates with the top of the transparent housing. Incense is placed within the cover assembly. A cap having a funnel shaped cavity with stem cavity communicates with the cover assembly. The cold air is warmed by the light bulb and passes upward through the cover assembly causing the liquids in the cup to be heated resulting in evaporation. The warm air engages the incense and passes outward from the lamp through the funnel cavity of the cap.

7 Claims, 6 Drawing Figures

INCENSE LAMP

SUMMARY OF THE INVENTION

My invention relates to a unique and novel lamp capable of providing fragrant odors.

It is known from U.S. Pat. Nos. 2,714,649; 2,742,342; and 3,080,624 that light means have been provided in vaporizers, but these aforementioned patents do not provide a means of transmitting the light means through their respective housings as well as being of unduly complicated design.

Accordingly, it is an object of my present invention to provide a lamp capable of providing a fragrant odor.

A further object of my present invention is to provide a means for holding said fragrant odor producing chemicals within the lamp.

A still further object of my present invention is to provide a means of warming the fragrant chemicals, wherein the chemicals are evaporated.

Yet, another object of my present invention is to provide a lamp of simple design and relatively low manufacturing cost.

Briefly, my present invention comprises a base communicating with an upward extending transparent housing. A light bulb and socket are mounted in a housing mounted onto the base, wherein the light socket housing is entirely disposed within the transparent housing. A power source with switch communicates with the electrical light socket. Air passage tubes allow passage of cold air into the chamber defined by the transparent housing. A cover assembly containing a liquid holding cup communicates with the top of the transparent housing. Incense is placed within the cover assembly. A cap having a funnel shaped cavity with stem cavity communicates with the cover assembly. The cold air is warmed by the light means and passes upward through the cover assembly causing liquids in the cup to be heated resulting in evaporation. The warm air engages the incense and passes outward from the lamp through the funnel cavity of the cup.

BRIEF DESCRIPTION OF THE DRAWINGS

The objects and features of the invention may be understood with reference to the following detailed description of an illustrative embodiment of the invention, taken together with the accompanying drawings in which.

DESCRIPTION OF THE PREFERRED EMBODIMENT

Figure 2:
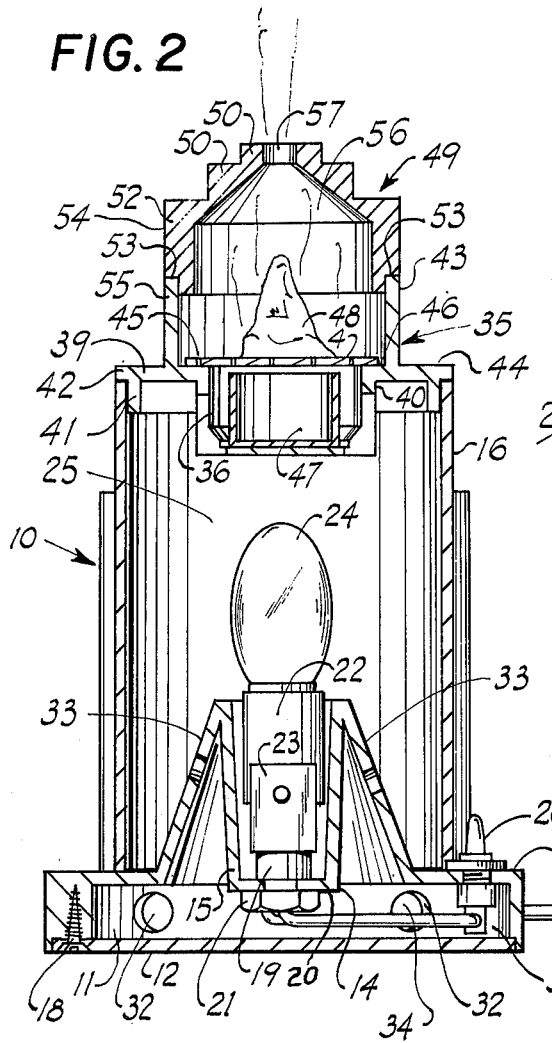
FIG. 2 illustrates a side cross sectional view of the lamp.

Turning now descriptively to the drawings, in which similar reference characters denote similar elements throughout the several views, FIG. 2 shows a modern incense lamp 10 consisting of a generally hollow cylindrical base 11 having a removable bottom face 12 and a permanent top face 13, wherein top face 13 has a central aperture 14 therethrough. An elongated open ended housing 15 mounted through aperture 14 extends upward from face 13 of base 11. An elongated transparent plastic cylindrical shaped housing 16 communicates with the top face 13 of base 11, wherein housing 16 extends upward from base 11.

Figure 1:
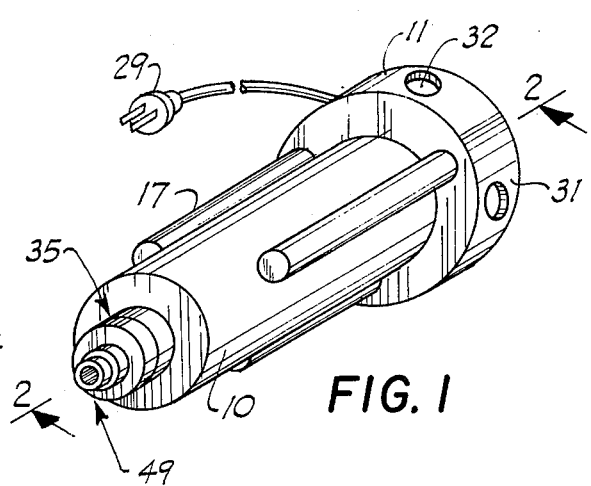
FIG. 1 illustrates a side perspective view of the lamp.
Figure 3:
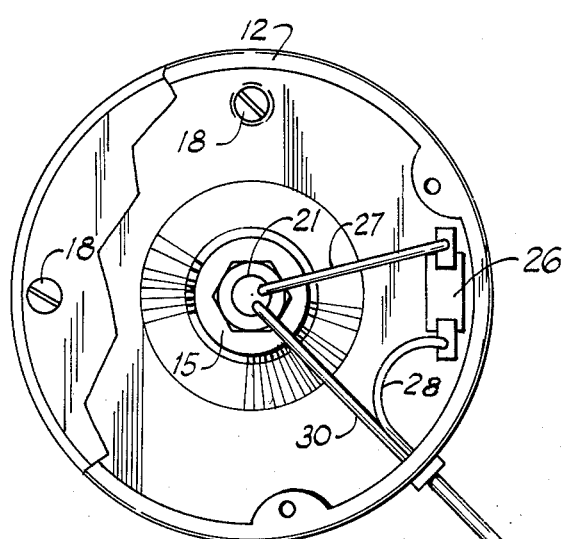
FIG. 3 illustrates a bottom cross sectional view of the lamp.

As shown in FIGS. 1 and 3, a plurality of post members 17 extend upward from base 11, wherein the posts 17 are secured to base 11 by a plurality of screws 18 passing upward through base 11. The posts 17 engage the outside periphery of housing 16 holding housing 16 onto base 11.

A vertically placed mounting member 19 contained within housing 15 as shown in FIG. 2 extends downward through the bottom open end 20 of housing 15. A nut 21 threads onto the bottom of member 19 engaging the bottom end 20 of housing 15. An electrical socket 22 communicates with the top end 23 of member 19 within housing 15. A light bulb 24 cooperates with socket 22, wherein the bulb 24 is contained within the chamber 25 of housing 16. An electrical push button switch 26 is mounted through top face 13 of base 11.

As shown in FIG. 3 the switch 26 is joined to socket 22 by a first wire 27 and to an electrical plug 29 by a second wire 28. Plug 29 and socket 22 are joined to each other by a third wire 30.

Referring back to FIG. 2, the sidewalls 31 of base 11 have a plurality of openings 32 therethrough. A plurality of open ended air tubes 33 affixed to the top outside periphery of housing 15 extend 45° downwardly through top face 13 of base 11, wherein the bottom open end 34 of tubes 33 communicate with openings 32.

Figure 5:
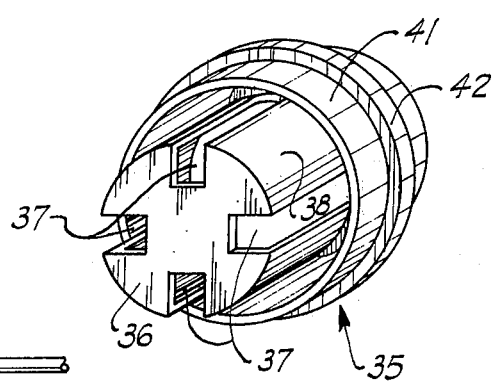
FIG. 5 illustrates an end view of the cover assembly of the lamp.

FIGS. 2 and 5 show the top cover assembly 35 of the lamp 10. The assembly 10 comprises an open top cylindrical member 36 having a plurality of longitudinal slot apertures 37 on the outside periphery 38 of member 36, wherein each aperture 37 transverses the entire length of member 36. An annular flange 39 is affixed to the top edge 40 of member 36. A first annular member 41 is affixed onto the outside periphery of flange 39. A second smaller annular member 42 is afixed onto the outside periphery of member 41. An upward extending cylindrical sleeve 43 communicates with the top center face 44 of flange 39. Second annular member 42 rest on top of housing 16.

Figure 4:
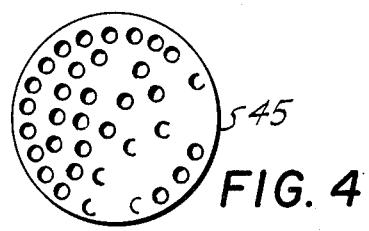
FIG. 4 illustrates a top view of the perforated disc.

A perforated disc member 45 as shown in FIG. 4 rest on the inner top edge 46 of flange 39 as shown in FIG. 2.

Figure 6:
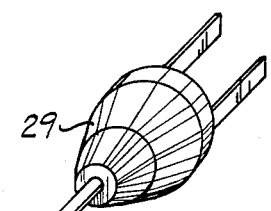
FIG. 6 illustrates an end view of the cup of the lamp.
Figure 6:
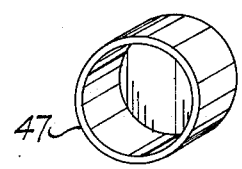

An open top cup member 47 for holding fragrances, liquids or medicals as shown in FIG. 6 is placed into member 36 below disc member 45 as shown in FIG. 2. A cone of incense 48 is placed on top of disc member 45. The top cap 49 resting on the cover assembly 35 consist of three open ended cylindrical tubes 50, 51, 52 of decreasing diameter stacked in a vertical alignment. The largest tube 52 rest on top of sleeve 43 by means of an annular aperture 53 contained on the bottom outside periphery 54 of tube 52, wherein aperture 53 engages the top edge 55 of sleeve 16. The inside of the cap 49 is formed in a funnel shaped cavity 56, wherein the stem 57 of the funnel cavity 56 corresponds to the inside cavity of the top smallest tube 50.

In the operation of the lamp 10, the bulb 10 transmits light through housing 16 as well as warming cool air flowing through air tubes 33 and openings 32 into chamber 25. The warmed air passes through slot aperture 37 heating up members 36, 47 causing the contents of member 47 to evaporate. The warm air passes upward through disc members 45 engaging incense 48.

The fragrant air passes upward through funnel cavity 56 out through stem 57 of cavity 56.

Hence, obvious changes may be made in the specific embodiment of the invention described herein, such modification being within the spirit and scope of the invention claimed, it is indicated that all matter contained herein is intended as an illustrative and not as limiting in scope.

Having thus described the invention, what I claim as new and desire to secure by Letters Patent of the United States is:

1. An incense lamp, which comprises:
   a. a hollow base having a removable bottom face;
   b. an upward extending transparent housing affixed to said base;
   c. a light means housing communicating with said base and disposed within said transparent housing;
   d. a light means mounted in said light means housing;
   e. a power means communicating with said light means;
   f. a cover assembly communicating with a top edge of said transparent housing;
   g. a first means of introducing air into said lamp;
   h. an open top cup for holding liquids contained in said cover assembly;
   i. said cover assembly having a plurality of slot apertures permitting upward passage of warmed air;
   j. a perforated disc member contained in said cover assembly above said cup member;
   k. a cap member communicating with said cover assembly; and
   l. said cap member having a funnel shaped air passage cavity allowing said warmed air to escape from said lamp.

2. An incense lamp as recited in claim 1, wherein said light means comprises a light bulb mounted in a light socket.

3. An incense lamp as recited in claim 2, wherein said power means comprises:
   a. a push button switch mounted in said base;
   b. said switch communicating with said socket; and
   c. an electrical plug communicating with said socket and said switch.

4. An incense lamp as recited in claim 3, wherein said first means comprises:
   a. said base having a plurality of opening therethrough;
   b. a plurality of open ended air passage tubes affixed to said light means housing communicating with said openings.

5. An incense lamp as recited in claim 4, wherein said cover assembly comprises:
   a. an open top cylindrical member having a plurality of said slot apertures;
   b. an annular flange affixed to a top edge of said open top cylindrical member;
   c. a first annular member affixed to the outside of said annular member affixed onto the outside periphery of said first annular member;
   d. an upper extending sleeve communicating with a top center face of said annular flange;
   e. said perforated disc member resting on said annular flange;
   f. said open top cup contained in said open top cylindrical member; and
   g. a second annular member resting on top of said transparent housing.

6. An incense lamp, as recited in claim 5, wherein said cap member comprises:
   a. three open ended cylindrical tubes of decreasing diameter stacked in a vertical alignment;
   b. a largest tube of said three tubes engaging said upper extending sleeve; and
   c. said three tubes having a funnel shaped cavity with a cavity stem.

7. An incense lamp as recited in claim 6, wherein incense is contained on top of said perforated disc member.

* * * * *